United States Patent [19]

Bradford et al.

[11] Patent Number: Plant 7,421

[45] Date of Patent: Jan. 15, 1991

[54] NECTARINE TREE (ROSE DIAMOND)

[76] Inventors: Norman G. Bradford, 11875 E. Savana Rd.; Lowell G. Bradford, 12439 E. Savana Rd., both of Le Grand, Calif. 95333

[21] Appl. No.: 457,184

[22] Filed: Dec. 26, 1989

[51] Int. Cl.[5] ..... A01H 5/00

[52] U.S. Cl. ..... Plt./41

[58] Field of Search ..... Plt./41

[56] References Cited

U.S. PATENT DOCUMENTS

P.P. 5,438 4/1985 Bradford ..... Plt. 41

*Primary Examiner*—James R. Feyrer

[57] ABSTRACT

The present invention relates to a nectarine tree and more particularly to a new and distinct variety broadly characterized by a medium size, medium vigorous, hardy, very productive and regular bearing tree. The fruit matures under the ecological conditions described in early June, with first picking on June 2, 1989, and is uniformly large in size, freestone in type, mostly red in skin color, mildly acidic and generously sweet in flavor, and firm in texture. The variety was developed as a hybridized seedling from the selected seed parent, Early Diamond (U.S. Plant Pat. No. 5,438), and an unnamed genetically dwarf peach seedling as the selected pollen parent.

1 Drawing Sheet

BACKGROUND OF THE NEW VARIETY

In a continuing effort to improve the quality of shipping fruits, we, the inventors, typically hybridize a large number of nectarine, peach, plum, apricot, and cherry seedlings each year. The present invention relates to a new and distinct variety of nectarine tree, which has been denominated varietally as "Rose Diamond". The present variety was hybridized by us in 1983, and the resulting seedling was planted in a cultivated area of our experimental orchard at Bradford Farms near Le Grand, Calif., in Merced County (San Joaquin Valley). Specifically, the hybridized seedling was originated by using Early Diamond (U.S. Plant Pat. No. 5,438) as the selected seed parent and an unnamed genetically dwarf peach seedling as the selected pollen parent. Subsequent to origination of the present variety of nectarine tree, we asexually reproduced it by budding and grafting, and such reproduction of plant and fruit characteristics were true to the original plant in all respects.

The present variety is similar to its selected seed parent, Early Diamond (U.S. Plant Pat. No. 5,438), by producing fruit that is almost fully red in skin color, freestone in type, firm in texture, and excellent in flavor, but is distinguished therefrom by producing fruit that ripens two days later, that is larger in size, and that is less prone to split-pitting.

DRAWING

The accompanying photograph exhibits three whole fruits positioned to display the characteristics of the skin color and form, one fruit halved around the suture to reveal the flesh and stone cavity, a stone that was cleaned and dried, and branches with leaves, all typical of the subject variety.

POMOLOGICAL CHARACTERISTICS

Referring now more specifically to the pomological characteristics of this new and distinct variety of nectarine tree, the following has been observed under the ecological conditions prevailing at the experimental orchard of the inventors near Le Grand, Merced County (San Joaquin Valley), Calif. All major color code designations are by reference to the Inter-Society Color Council, National Bureau of Standards. Common color names are also used occasionally.

TREE

Size: Medium.
Vigor: Medium.
Growth: Spreading and dense.
Form: Vase formed.
Hardiness: Hardy.
Production: Very productive.
Bearing: Regular bearer.
Trunk:
- *Size.*—Medium.
- *Texture.*—Medium.
- *Color.*—Grayish reddish brown [46. gy.rBr].
- *Lenticels.*—Numerous. Color: Light yellowish brown [76. l.yBr]. Average Size: 3/16" [4.8 mm.].

Branches:
- *Size.*—Medium.
- *Texture.*—Medium.
- *Color.*—1st year wood — Topside: Light grayish red [18. l.gy.R] if exposed to sunlight. 1st year wood — Underside: Brilliant yellow green [116. brill.YG]. Older wood: Deep yellowish brown [75. deep yBr].
- *Lenticels: Numerous, small.*

Leaves:
- *Size.*—Large. Average length: 5½" [139.7 mm.]. Average width: 1¼" [31.8 mm.].
- *Thickness.*—Medium.
- *Form.*—Elliptical.
- *Apex.*—Acuminate.
- *Base.*—Acute.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Petiole.*—Average length: ½" [12.7 mm.]. Average thickness: 1/16" [1.6 mm.].

*Glands.*—Numbers: Mostly 2 to 4 per leaf. Position: Some oppositely and some alternately positioned on petiole and base of blade. Size: Small. Form: Globose. Color: Moderate greenish yellow [102. m.gY].

*Stipules.*—Numerous. Average length: ¼" [6.4 mm.].

Flower buds:

*Hardiness.*—Hardy.

*Size.*—Medium.

*Length.*—Medium.

*Form.*—Free.

*Surface.*—Pubescent.

Flowers:

*Blooming period.*—Early, as compared with other varieties.

*Size.*—Large, with an occasional double blossom.

*Color.*—Varies from pale pink [7. p.Pk] to moderate pink [5. m.Pk].

FRUIT

Maturity when described: Hard but eating ripe, June 4, 1989.

Date of first picking: June 2, 1989.

Date of last picking: June 8, 1989.

Size: Uniform, large.

*Average diameter axially.*—2½" [63.5 mm.].

*Average traversely in suture plane.*—2⅜" [60.3 mm.].

Form: Uniform, symmetrical, globose to slightly oblong.

*Longitudinal section form.*—Round to slightly oval.

*Transverse section through diameter.*—Round.

Suture: A shallow depression extending from the base to the apex with a slight depression on both sides of the pistil point.

Ventral surface: Rounded slightly, lipped toward the apex on both sides.

Lips: Mostly equal.

Cavity: Flaring, circular, suture showing on one side.

Base: Cuneate and slightly truncate.

Apex: Rounded and slightly depressed.

Pistil point: Negligible in length, depressed within the suture.

Stem: Medium size.

*Average length.*—¼" [6.4 mm.].

*Average width.*—⅛" [3.2 mm.].

Skin:

*Thickness.*—Medium.

*Texture.*—Tough.

*Tenacity.*—Tenacious to flesh.

*Tendency to crack.*—None observed as of yet.

*Color.*—From dark red [16. d.R] to moderate red [15. m.R] over a light orange yellow [70. l.OY] background with some brilliant yellow [83. brill.Y] freckling near the apex.

Flesh:

*Color.*—Brilliant yellow [83. brill.Y] to the pit with a slight amount of deep pink [3. deep Pk] flecking very near the stone apex.

*Stone cavity color.*—Light yellow [86. l.Y].

*Amygdalin.*—Scarce.

*Juice.*—Abundant, rich.

*Texture.*—Firm, tough, meaty.

*Fibers.*—Abundant, fine.

*Ripens.*—Mostly even, but slightly earlier at the apex.

*Flavor.*—Mildly subacid and generously sweet.

*Aroma.*—Slight.

*Eating quality.*—Very good to best.

STONE

Type: Freestone.

Form: Oval.

Base: Straight.

Apex: Acute.

Sides: Equal.

Surface: Irregularly furrowed more toward the apex, with scattered pitting mostly toward the base.

Ridges: Rounded.

Color: Moderate orange yellow [71. m.OY].

Pit wall: 3/16" [4.8 mm.] thick.

Tendency to split: Slight.

Kernel:

*Form.*—Oval.

*Taste.*—Sweet.

*Viable.*—Yes.

*Average width.*—½" [12.7 mm.].

*Average length.*—¾" [19.1 mm.].

Pellicle color: Moderate orange yellow [71. m.OY].

Amygdalin: Scant.

USE

Market: Fresh market, both local and long distance shipping.

Keeping quality: Very good.

Shipping quality: Very good.

Resistance to insects: No unusual susceptibilities noted.

Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of freestone nectarine tree, substantially as illustrated and described, which most closely resembles its seed parent, Early Diamond (U.S. Plant Pat. No. 5,438), by producing fruit that is almost fully red in skin color, freestone in type, firm in texture, and excellent in flavor, but is distinguished therefrom and an improvement thereon by producing fruit that ripens two days later, that is larger in size, and that is less prone to split-pitting.

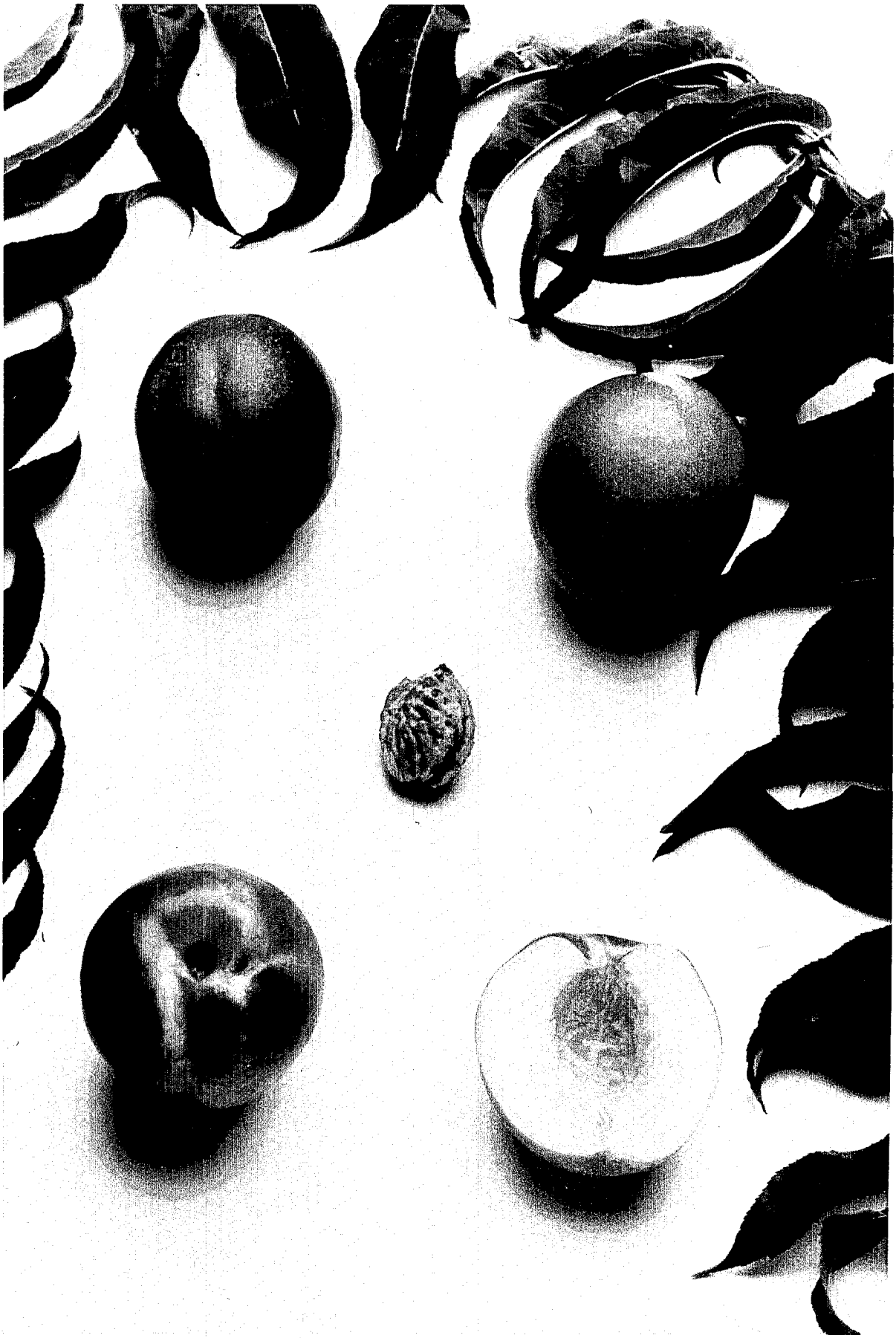

* * * * *